US000001310H

United States Statutory Invention Registration [19]

[11] Reg. Number: H1310

Peterson et al.

[43] Published: May 3, 1994

[54] PROCESS FOR MEASURING LOW CADMIUM LEVELS IN BLOOD AND OTHER BIOLOGICAL SPECIMENS

[75] Inventors: David P. Peterson, Orland Park; Edmund A. Huff, Lemont; Maryka H. Bhattacharyya, Naperville, all of Ill.

[73] Assignee: The United States of America as represented by the United States Department of Energy, Washington, D.C.

[21] Appl. No.: 647,074

[22] Filed: Jan. 29, 1991

[51] Int. Cl.[5] ..... G01N 33/20

[52] U.S. Cl. ..... 436/74; 436/81; 436/178

[58] Field of Search ..... 436/74, 81, 125, 178; 423/100; 210/662, 684

[56] References Cited

U.S. PATENT DOCUMENTS 4,080,171 3/1978 Sano et al. ..... 436/172

OTHER PUBLICATIONS

"Simultaneous determination of lead and cadmium in blood and urine by coupling ion exchange resin chromatography and atomic absorption spectrophotometry", Arch, Mal. Prof., 1972, 33 No. 3, Mar.

Korkisch, J. et al., *Talanta,* vol. 21, No. 10, pp. 1035–1046 (1974).

Hayashita, T. et al., "Extractive Permeation of Zinc(II) and Cadmium(II) Chloride Complexes through Anion-Exchange Membrane" *Bulletin Chemical Society of Japan,* vol. 63, pp. 576–580 (1990).

Westerlund-Helmerson, "Determination of Lead and Cadmium in Blood by a Modification of the Hessel Method" *Atomic Absorption Newsletter,* vol. 9, pp. 133–134 (1970).

Borin, L. L. et al., "Calculation of the activities of resinates in systems with sorption of metal complexes by anion exchangers" Chemical Abstracts, vol. 98, abstract 96236d (1983).

Asambadze, G. et al., "Polarographic study of the kinetics of anion exchange of chloride complexes of zinc and cadmium" Chemical Abstracts, vol. 72, abstract 32831z (1970).

Chen, H., "Analytical characteristics of zincon-loaded resin and its applications" Chemical Abstracts, vol. 114, abstract 156141e (1991).

*Primary Examiner*—Robert L. Stoll
*Assistant Examiner*—Joseph D. Anthony
*Attorney, Agent, or Firm*—James W. Weinberger; Thomas G. Anderson; William R. Moser

[57] ABSTRACT

A process for measuring low levels of cadmium in blood and other biological specimens is provided without interference from high levels of alkali metal contaminants by forming an aqueous solution and without contamination by environmental cadmium absent the proteins from the specimen, selectively removing cadmium from the aqueous solution on an anion exchange resin, thereby removing the alkali metal contaminants, resolubilizing cadmium from the resin to form a second solution and analyzing the second solution for cadmium, the process being carried out in a cadmium-free environment.

9 Claims, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

PROCESS FOR MEASURING LOW CADMIUM LEVELS IN BLOOD AND OTHER BIOLOGICAL SPECIMENS

CONTRACTUAL ORIGIN OF THE INVENTION

The U.S. Government has rights in this invention pursuant to Contract No. W-31-109-ENG-38 between the U.S. Department of Energy and the University of Chicago representing Argonne National Laboratory.

BACKGROUND OF THE INVENTION

This invention relates to the measurement of cadmium in biological specimens and more particularly to the detection and measurement of ultratrace cadmium levels in blood and other biological fluids.

Measurement of cadmium in blood, urine, tissue and other biological specimens at low levels is important for a number of reasons. Cadmium has a long biological half-life and the toxic effects of exposure are cumulative. Chronic exposure to cadmium can irreversibly damage the kidneys. Cadmium is now considered to be a potential carcinogen. Also, recent biomedical research suggests that low-level cadmium exposure from smoking may contribute to osteoporosis.

Cadmium in addition to lead may be found in the working environment, in ambient air, in drinking water, in tobacco smoke and in food. Certain foods may be the major contributors to human exposure to cadmium. Smoking may be an additional significant source of cadmium exposure. Because cadmium accumulates in humans from different sources, biological monitoring has become recognized as a desired way to estimate the total exposure and risks associated with cadmium.

The measurement of the level of toxic metals in human body fluids is often the best way of evaluating undue exposure, whether the source be industrial, environmental or iatrogenic. To be of any use in diagnosing and monitoring exposed individuals, analytical results generated must be reliable (i.e., accurate), and reproducible with time.

The determination of cadmium in biological samples is of considerable interest to health and research organizations. Studies have been conducted to measure and monitor cadmium (and other toxic substances) in body fluids. One study, as reported in "An Interlaboratory Comparison Programme For Several Toxic Substances in Blood and Urine" by Jean-Philippe Weber, in The Science of the Total Environment, (1988) 71, 111–123, was directed to the measurement of cadmium (and other toxic substances) in blood and urine as performed by a number of laboratories. Consistency in the measurements of cadmium even at levels above 5 μg/L was difficult as indicated by the reported coefficients of variation in the order of 30–40%, with higher values for lower concentrations.

The most widely used analytical technique for measuring cadmium in blood and urine samples involves the steps of deproteination and direct analysis by electrothermal atomic absorption spectrophotometry (ETAAS). In general, this technique has provided acceptable consistency of results with samples having a cadmium concentration above about 5 μg Cd/L.

One reason for the difficulty in measuring cadmium at levels of ≦5 μg/L is that the deproteination or wet-ashing step in the above described technique removes cadmium from its organic environment but does not separate it from inorganic constituents. Sodium and potassium concentrations in normal blood are generally $10^6$ times greater than cadmium. When using electrothermal atomic absorption spectrophotometry (ETAAS) with deuterium background correction for the analysis of cadmium in blood, this inorganic environment contributes significantly to the inaccuracy and imprecision of the measurement. Another difficulty associated with measuring cadmium in blood arises from the presence of cadmium as an ubiquitous environmental contaminant. Control or avoidance of cadmium contamination by glassware, plastic ware, reagents and air is of utmost importance for proper accuracy.

In order to evaluate cadmium exposures in an environmental setting, it is important to measure cadmium at low levels (i.e., below about 0.5 μg/L) in blood, urine and other biological specimens. Seawater is also an important medium for measuring cadmium content since cadmium may have an adverse effect on developing fish embryos. Data on cadmium levels, particularly in body fluids, and changes in those levels related to exposure to special environmental conditions, could be of considerable importance in providing early indications of medical problems. Since the toxic effects of exposure are reported to be cumulative, information of this type could also be particularly important in association with tests on young persons to determine early adverse exposure.

Accordingly, one object of this invention is a method of testing biological specimens for low cadmium concentrations. Another object of the invention is a method of testing biological fluids containing high values of alkali metal contaminants for cadmium. Yet another object of the invention is a method for testing biological fluids for low cadmium concentration with improved accuracy. These and other advantages of the invention will become apparent from the following description.

SUMMARY

Briefly, the invention is directed to the measurements of cadmium in biological fluids containing levels of alkali metal contaminants which would interfere with accurate measurements for cadmium and more particularly to measurements in body fluids such as blood, plasma and urine at cadmium levels below about 5 μg/L. The measurement is carried out by the steps of forming an aqueous solution having an acid pH and essentially free of insolubles from the biological fluid with HCl to convert the cadmium to an anioninc cloride selectively removing cadmium from the aqueous solution on an anion exchange resin, resolubilizing cadmium from the resin to form a second solution and analyzing for cadmium in the second solution advantageously by electrothermal atomic absorption spectrophotometry. It is important that the environment including the reagents, column with anion exchange resin and process equipment such as glass and plasticware be essentially cadmium-free (i.e., contributing a total of less than about 0.1 ng Cd to the assay) and that the processing of the samples be carried out under a hood to reduce air contaminants.

For particularly low cadmium concentrations (i.e., below about 0.5 μg/L), the invention advantageously includes the step of increasing the cadmium content of the second solution by depositing cadmium on the resin from a larger volume of the first solution. By this technique, a cadmium concentration of 0.2 μg/L associated with the first aqueous solution may be increased to about 0.8 μg/L by contacting the resin with 8 mL of the first solution and resolubilizing the cadmium into 2 mL of the second solution for analysis.

Since it is important to use reagents and equipment essentially Cd-free, the invention also includes a kit comprising the reagents, equipment, one or more packages containing the reagents and equipment in an essentially cadmium-free environment with instructions descriptive of the method of the invention.

The separation of cadmium on the anion exchange resin will also normally include zinc which has a chromatographic behavior similar to cadmium. Since the signal from the ETAAS is reduced by the presence of zinc, the invention includes a corrective factor in the standards and the sample to offset the effect of zinc.

The invention has a number of advantages. Measurements of cadmium concentrations in the order of 0.2 μg/L may be carried out with acceptable accuracy and lack of contamination by Cd in the atmosphere. These measurements are also associated with improved reliability based on the coefficient of variation (CV). Use of the invention typically will remove about 97 wt. % of the contaminants from a sample of blood while providing a solution for cadmium analysis containing greater than 94 wt. % of the original cadmium.

DETAILED DESCRIPTION OF THE PREFERRED EMBODIMENT

Figure 1:
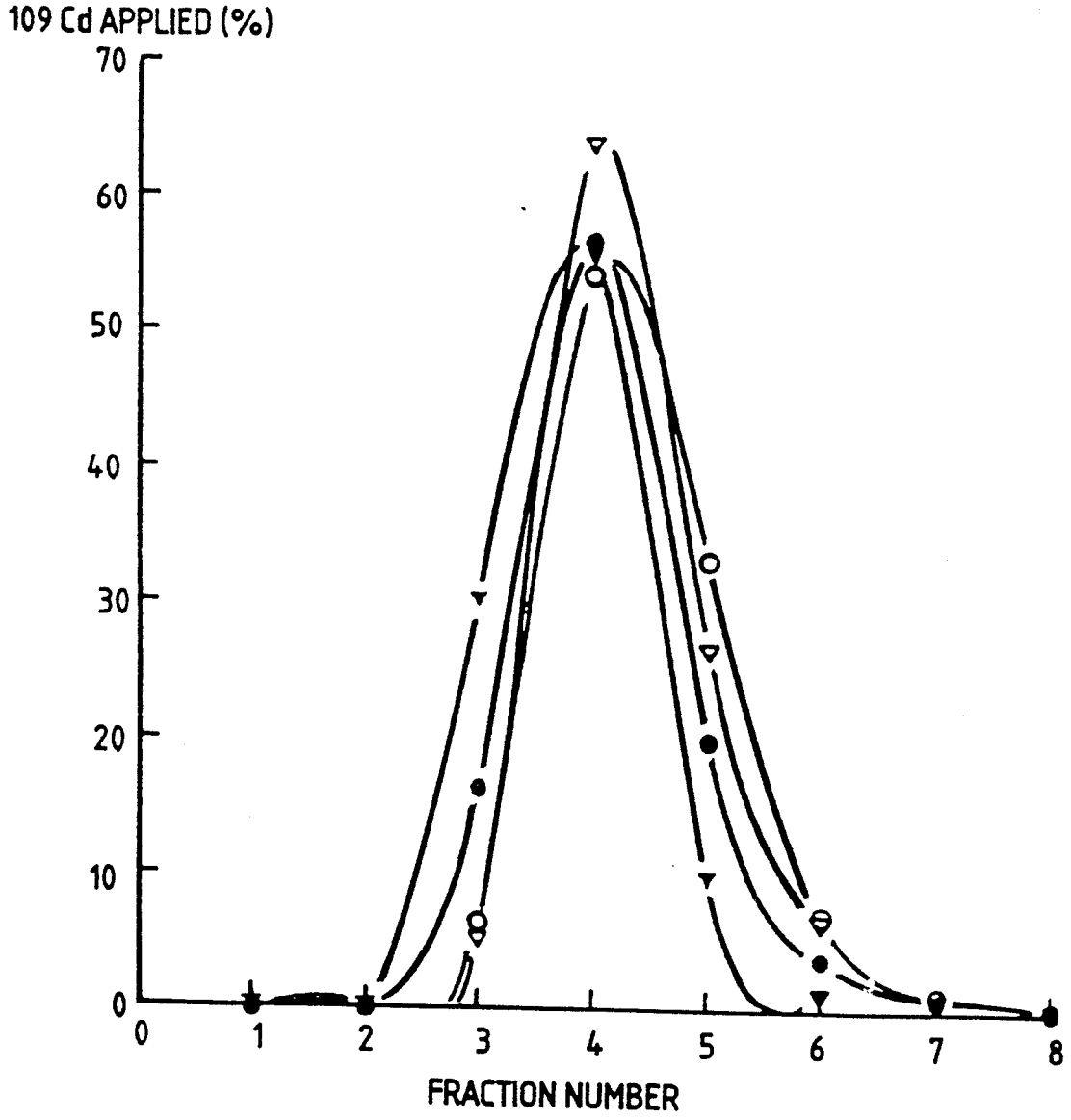
FIG. 1 is an elution profile of $^{109}Cd$ separated from whole blood (●), plasma (▽), urine (▼), and pure acids (o).

The invention is particularly useful to carry out measurements of cadmium in biological samples and particularly those associated with body fluids such as blood, urine and the like. For simplification, the following description will be directed to measurement in samples of blood, plasma and urine. However, it should be recognized that analysis of other biological samples of cadmium in such fluids as seawater may be conducted with the described technique without undue experimentation.

The process for measuring cadmium in the samples primarily involves the steps of forming an aqueous salt solution with HCl to convert the cadmium to an anionic chloride, the solution including any inorganic contaminants from the sample, selectively removing cadmium from the solution on an anion exchange resin, resolubilizing cadmium on the resin to form a second solution and analyzing the second solution to provide a value representative of the cadmium content in the sample.

In the process, cadmium is separated from the primary contaminants prior to the analysis. These contaminants are principally inorganic and especially the alkali metal contaminants at significant levels in the body fluid. Advantageously, the invention will provide a solution for analysis in which greater than 99 wt. % of the alkali metal contaminants have been removed and a background absorption unit with respect to the analysis below 1 unit. Table I below provides a representative blood composition before separation and the cadmium sample after separation. As shown, zinc remains with the cadmium.

TABLE I

Concentrations of Cadmium and Major Elements in the Supernatant of Deproteinated Whole Blood and in the Cadmium Fraction After Anion-Exchange Separation

| | Deproteinated Blood (μg/ml) | Cadmium fraction (μg/ml) |
|---|---|---|
| Ca | 13.4 | 0.01 |
| Cu | 0.16 | <0.01 |
| Fe | 3.3 | 0.1 |
| K | 625 | 0.5 |
| Mg | 11.0 | <0.01 |
| Na | 505 | 0.5 |
| Zn | 1.43 | 1.47 |
| Cd | 0.00014 | 0.00013 |

Since the contaminants are removed prior to the analysis, testing of blanks and standards by ETAAS provide extremely low reference levels. Under these circumstances, detection limits in the order of 0.01–0.2 μg Cd/L may be achieved depending on the particular fluid and sample size. The detection limit is defined as 3×SD (standard deviation) of the blank value.

The process is also capable of measuring cadmium at low levels in the biological samples with reasonable precision. The coefficient of variation (CV) is used as a measure of precision in the tests and is defined as the standard deviation/mean as a percentage. Based on 2 ml samples, measurements of cadmium at levels from 1 μg Cd/L and above and particularly 1–5 μg Cd/L provide CV values of 15–20% and below for about 3 replicate analyses. For cadmium contents in the general range of 0.3–1.0 μg Cd/L, CV values are generally in the order of 20% and below for about 3 analyses. For low values of 0.05–0.3 μg Cd/L, CV values will generally be greater than 20% although generally below about 25%. At these low values, larger sample volumes (i.e., 4 ml or 8 ml) may be used with the CV values being reduced to about 20–25%. In general, CV values below about 25% are achieved by use of the invention.

In the process, it is important that the samples be prepared in a Cd-free environment which limits the external cadmium effect in the assay to a total of about 0.1 ng Cd, particularly when cadmium concentrations are below about 0.1 μg Cd/L. This requires the use of extremely pure water and acids having cadmium concentrations well below 1 ppb. Acid-washed glassware and metal-free plasticware are also used. Sample preparation is under a Class 100 hood. Gloves are used in handling the requipment and the test tubes are covered during transfer. A plastic cover is provided over the ETAAS unit. In addition, it is usually desirable to run a blank and test standard every three samples to check the ETAAS for calibration and accuracy.

The use of a $^{109}Cd$ "spike" may be useful in the analysis technique to increase the sensitivity of the assay. FIG. 1 shows the general distribution of $^{109}Cd$ from five different portions (1 ml) of a sample prepared with $^{109}Cd$ on the anion exchange resin. As shown, about 55 wt. % of $^{109}Cd$ is in the second portion (or second ml) of the sample. In testing for cadmium in a sample, $^{109}Cd$ may be added to the sample, and a selected portion eluted from the anion exchange resin may be analyzed, with the measured value of the stable cadmium (other than $^{109}Cd$) increased by a factor equal to $^{109}Cd$ added/$^{109}Cd$ in the analyzed portion. The result will be an increase in assay sensitivity.

Figure 2:
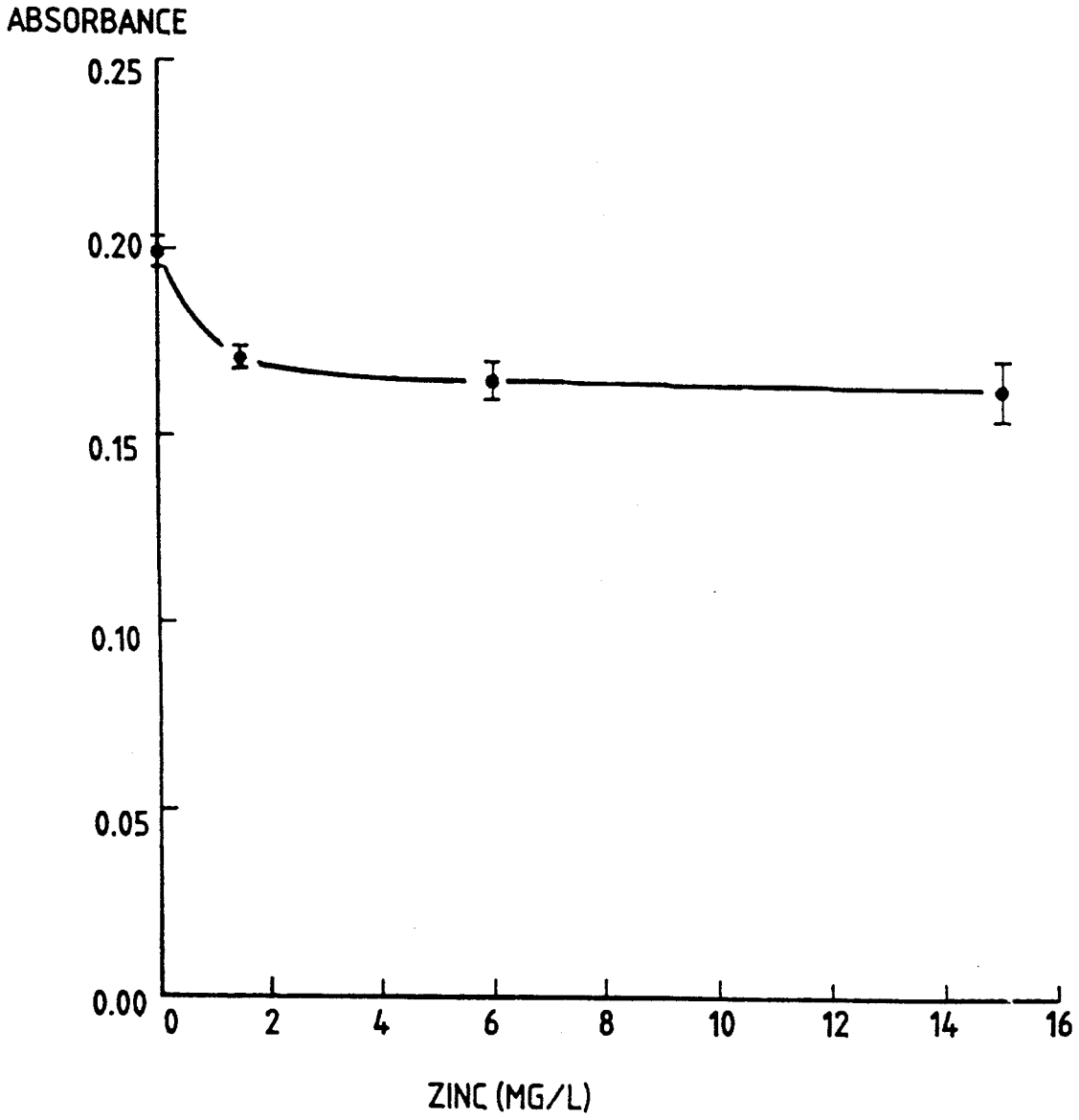
FIG. 2 is a graph showing the effect of zinc on the peak area absorbance of cadmium using ETAAS analysis.

In contrast to the other contaminants, zinc is also deposited on the resin and requires a corrective factor to obtain an accurate value for cadmium. FIG. 2 shows the effect of zinc on the measurements, with a value of about 1.4–1.5 mg Zn/L and above requiring an increase in the order of 14–18%. Advantageously, the presence and content of zinc in a sample is separately determined by flame atomic absorption or the like prior to the cadmium analysis with the appropriate Zn being added to the blank and standard fluids used in calibrating the ETAAS unit and for comparison purposes.

Since this process is capable of concentrating low concentrations of Cd in biological fluids, the routine measurement of plasma Cd concentrations has become possible. Recent Cd exposure (within 12–24 hours) appears as an increase in plasma Cd concentrations. By 24 hours after a single subcutaneous exposure, nearly all of the Cd in blood is bound within the blood cells. The ratio of Cd in plasma to Cd in whole blood therefore provides a measure of a person's very recent exposure. The plasma Cd concentration is important because Cd in plasma, rather than that bound to blood cells, is generally believed to be responsible for the delivery of Cd to peripheral organs such as kidney, liver, and bone.

The results of plasma and blood Cd measurements in beagles exposed to 15 ppm Cd in water using this process are shown in Table II below. The ratios of plasma/blood Cd are shown in the last column and range from 2.6–16.5%. One likely benefit of determining the plasma/blood Cd ratio will be its use by scientists studying Cd to provide new insights for dose-response relationships and the mechanism of Cd toxicity to various organs.

TABLE II

Cadmium Concentration (μg/liter) in Plasma (Cd-P) Versus Blood (Cd-B) of *Canis familiaris* Exposed to Cadmium in Water

| Sample | Cd-$P_E$ | Cd-$P_H$ | Cd-B | Cd-$P_H$/Cd-B |
|---|---|---|---|---|
| A | 0.72 | 0.46 | 8.98 | 0.051 |
| B | 2.35 | 2.46 | 21.98 | 0.112 |
| C | 0.96 | 1.37 | 8.87 | 0.154 |
| D | 1.87 | 1.98 | 11.98 | 0.165 |
| E | 1.58 | 1.13 | 13.71 | 0.082 |
| F | 0.48 | 0.57 | 12.12 | 0.047 |
| G | 0.48 | 0.52 | 19.58 | 0.026 |

Advantageously, the analysis for cadmium is by an atomic absorption technique and preferably by electrothermal atomic absorption spectrophotometry (ETAAS). The principle of this technique is based upon the absorption of light at element-specific wavelengths (resonance line) for neutral atoms in the ground state. Solutions containing cadmium are placed onto a piece of pyrolytically coated graphite and dried. The graphite is heated very quickly by passing an electrical current across it. When the temperature of the graphite reaches the boiling point of the element or a salt of it, the element forms a gaseous cloud in the light path. The amount of light that is absorbed is proportional to the quantity of ground state neutral atoms formed from the element deposited onto the graphite. Absorption of light by other elements or molecules in the gas cloud produced during atomization (background absorbance) can introduce significant errors in the analysis. For this reason, a second beam of light is passed through the atomic vapor to measure light absorption due to the background material. This procedure is called deuterium background correction and works well when background absorption is kept below 1.0 absorbance unit. A more sophisticated form of background correction is available which has been reported to be capable of correcting background absorbances greater than 2.0 absorbance units. It is called Zeeman background correction and uses strong magnetic fields to intermittently polarize the light. In practice, atomic absorption spectrophotometers are calibrated with known standards so that the absorbance readings obtained from unknown samples can be directly converted to concentration units.

Particularly with body fluids of low cadmium content, the process advantageously includes a step of increasing the cadmium content in the solution (second solution) of resolubilized cadmium. A larger sample of the body fluid may be used to provide a larger volume (i.e., 8 ml) of the aqueous solution used to treat the anion exchange resin. The cadmium would then be resolubilized in a 2 ml solution with the cadmium content being increased by a factor of four permitting more accurate analysis.

In carrying out the test procedures associated with the invention, it is particularly important that the reagents, the glass and plastic ware and the samples are free from contamination by cadmium in the air, water, or other sources. The assay requires extremely pure water and concentrated acids having cadmium concentrations well below 1 ppb. Equipment used for the analysis of cadmium in blood includes a standard atomic absorption spectrophotometer equipped with electrothermal atomization and deuterium background correction, centrifuge, laminar flow hood or equivalent quality air, properly acid-washed glassware and plasticware, and liquid measurement devices capable of accurate and precise measurements in the range of 5 μl to 10 ml and anion exchange columns. Advantageously, Cd-free equipment is provided as a kit with a package or packages to avoid contamination and instructions. Representative instructions are as follows:

KIT INSTRUCTIONS

Special Precautions

Three reagents in this kit contain corrosive acid (hydrochloric acid, nitric acid, and sulfuric acid) and should be handled with the proper protective equipment (i.e., rubber gloves, laboratory coat, safety goggles). During all manipulations, the samples should be protected from airborne cadmium contamination by working in a Class 100 air safety hood or by covering the samples with screw caps or cadmium-free plastic wrap. Because cadmium is a ubiquitous environmental contaminant, painstaking care must be taken to avoid cadmium's introduction from such sources as air, handling, and glassware. Cigarette smoke contains cadmium, and this analysis should not be attempted unless the laboratory environment is smoke-free. Samples should be handled using rubber gloves that have been rinsed with deionized water. Any plasticware (i.e, pipette tips, beakers, etc.) should be demonstrated free from cadmium contamination or should be rinsed with dilute nitric acid followed by a deionized water rinse. Glassware used should be leached in approximately 1N $HNO_3$ overnight, rinsed with cadmium-free water, dried and covered with plastic wrap to prevent airborne contamination. Special attention should be paid to the way the sample is collected. Vacutainers used for blood draw and storage should be tested routinely for cadmium contamination. Although the stainless-steel needles used for blood collection are an unlikely source of contamination, they should be tested if all other sources of contamination have been ruled out.

Kit Contents:

Reagents:

(1) 170 ml conc $HNO_3$
(2) 250 ml conc HCl
(3) 10 ml 10% $H_2SO_4$
(4) 1 gal. (3.7 L) ultra-pure $H_2O$
(5) 2 ml of Zn standard (1000 μg/ml,Cd-free)

Components:

(1) 55 g Anion Exchange resin
(2) 100 glass frits
(3) 50 polypropylene chrom columns
(4) 160 15 ml metal-free centrifuge tubes with screw cap Equipment needed (but not supplied):

1. Centrifuge which will hold 15 ml centrifuge tubes and provide centrifugal force of approximately 1300×g.
2. Pipetting devices which use disposable plastic tips and are capable of delivering volumes in the range of 20 μl–10 μl with good precision.
3. Source of Class 100 air (HEPA filtered air, such as obtained from a biological safety cabinet).
4. Cd-free plastic pipette tips (polypropylene tips without any dye added to the formulation will normally suffice; some manufacturers offer metal-free plastic products, such as Elkay Products, Inc., Shrewsbury, Mass.).
5. Atomic Absorption Spectrophotometer equipped with electrothermal atomization.

The process for measuring cadmium in blood or other biological material requires a sample of a body fluid such as blood, plasma or urine. Extraction of cadmium is carried out by diluting the whole blood with high resistance water and removing proteins and fat by the addition of nitric acid followed by centrifugation. Nitric acid is preferred over hydrochloric since hydrochloric might attack the protein content of the sample. The resultant supernatant liquid contains cadmium in the remaining inorganic salts. This supernatant is further acidified with 2N HCl to convert the cadmium to an anionic chloride. In the next step, cadmium is separated from the remaining salts using anion exchange chromatography. Cadmium behaves as an anion in 2N HCl and is bound tightly by a strong anion exchange resin. The remaining salts in biological specimens such as sodium, potassium, calcium, magnesium, do not form anions and pass through the anion exchange column. Cadmium and zinc (and possibly mercury) bind to the columns and are eluted in a small volume of 1N $HNO_3$ with 100% recovery of the cadmium. These may be referred to as metals in column 2b of the Periodic Table with atomic weights of 30–80. Column elution is thus a simple two-step batch process. The 2N HCl step concentrates the cadmium on the top of the anion exchange resin, allowing as much sample to be applied as needed to achieve the desired sensitivity. For example, increasing the sample from 2 ml to 8 ml can increase the measurement limit by a value in the order of 10 times. In this manner, detection limits in the order of 0.2 ppb Cd may result in lower values of 0.02 ppb Cd. Following the column elution, the cadmium released from the column in a nearly salt-free solution is concentrated in a small volume in preparation for analysis. Sulfuric acid is added to the column eluate to a level of 0.1% (vol/vol) in order to reduce the volatilization of cadmium in the analysis step. Cadmium is then analyzed by standard atomic absorption analysis using electrothermal atomization with deuterium background correction.

Accordingly, the invention may be considered as a process for analyzing cadmium in biological specimens by a combination of steps which include extracting cadmium and other water soluble salts in a water solution, separating cadmium from essentially all of the other salts by the use of an anion exchange resin and detecting cadmium in the remaining solution by atomic absorption analysis. Advantageously, the invention utilizes a zinc correction to compensate for the reduced signal caused by the presence of zinc. Also, advantageously, the invention includes a kit which includes acid reagents with levels of cadmium below 1 ppb, high resistance water with cadmium content below 1 ppb, glass and plastic vessels having cadmium content below 1 ppb, and within appropriate packaging containing instructions.

The algorithm used to convert the concentration of the cadmium-containing fractions after anion exchange back to cadmium concentration for a sample is described below. Typically, the volume from the column is 5 ml and the initial volume of the sample is 2 ml. The algorithm is applicable to the analysis of samples of blood, plasma and urine.

| | |
|---|---|
| Cd (analyzed) ng/ml × volume* = ng Cd recovered (R) | [1] |
| ng $Cd_{(R)}$ × 6/5 (dilution by HCl) × 8/5 (reciprocal fraction of aqueous solution-SN1) = ng Cd corrected | [2] |
| ng Cd corrected divided by (initial volume of sample used) = ng Cd/ml = ppb | [3] |

*volume collected from anion exchange column

The following examples are provided for illustrative purposes and are not intended to be restrictive as to the scope of the invention:

EXAMPLES I–III

Samples of blood from a human donor were analyzed for cadmium content. In the test, each sample of whole blood was diluted 1:4 (2 mL whole blood+6 mL 1N $HNO_3$) in Cd-free test tubes (either acid washed glass or metal free polypropylene) and vortexed for 30 sec. After standing for about 15 min., the samples were centrifuged for about 10 min. at 1300×g. The samples were covered to prevent airborne contamination. After centrifugation, the surface fats and lipoproteins were removed by adsorption to plastic pipette tips prior to pipetting the first supernatant (SN1). In preparation for column chromatography, 5 mL of a deproteinated SN1 was transferred to a clean test tube and 1.0 mL of 12.8M hydrochloric acid was added. The samples were vortexed again. After a second 10-min. centrifugation at 1300×g (to remove any suspended particulates), a 5 mL sample (SN2) was added directly to the equilibrated anion exchange column. This resin was identified by the supplier, BIO-RAD Laboratories of Richmond, Calif., as a strongly basic anion exchanger with quaternary ammonium functional groups attached to the styrene divinylbenzene copolymer lattice. It is further identified as an AG1 resin which is resistant to oxidation. The column was rinsed with 3 mL 2N HCl. Cadmium was eluted or resolubilized from the column with 1N $HNO_3$. The first 2 mL went to waste (based on a pretest determination that the first 2 mL advanced the cadmium to the bottom of the column), and the following 5 mL were collected in an acid-cleaned borosilicate test tube for cadmium analysis. Five microliters of concentrated sulfuric acid was added to prevent loss of Cd as $Cd(NO_3)$ during drying or ashing. Original sample volumes at 2 ml, 4 ml and 8 ml were subjected to the above assay steps and were analyzed for cadmium by electrothermal atomic absorption spectrophotometry (ETAAS).

The analysis by ETAAS was carried out by the conventional technique as described previously. The technique is also described in Stoeppler and Brandt (1980), Fresenius Z. Anal. Chem. 300, 372-380. Compensation for background was provided by deuterium background correction. The instrument was calibrated with known standards for cadmium. Since the presence of zinc affected the peak area absorbance of cadmium analyzed by ETAAS, zinc was added to the standards used to generate the standard curve for cadmium analysis. The cadmium concentration of unknown samples was compared to standards prepared in 1N $HNO_3$, 0.1% $H_2SO_4$ v/v, and containing 1-6 mg Zn/L.

The test results for blood are shown in Table III below. As shown, three 2 mL samples were analyzed for cadmium with the results being 0.57±0.004 μg/L and a CV of 10%. For the two 4 mL samples, the results were 0.62±0.05 μg/L and a CV of 8%. For the 8 mL samples, two samples provided consistent values of 0.45±0.02 μg/L with a CV of 6%. One 8 mL sample tested at 0.72 μg/L with the significant difference being attributed to operation of the furnace associated with the ETAAS test (spurious contamination). The CV for the three samples was 30%.

TABLE III

Effect of Blood Sample Volume on Cadmium Recovery

| Sample volume | Cadmium concentration (μg/liter) | CV (%) |
|---|---|---|
| 2 ml | 0.57 ± 0.04(3) | 10 |
| 4 ml | 0.62 ± 0.05(2) | 8 |
| 8 ml | 0.54 ± 0.16(3) | 30 |

The results show that in general the concentration obtained is essentially independent of sample volume, particularly at concentrations in the order of 0.10 μg Cd/L and above.

EXAMPLES IV-VI

Plasma samples were analyzed using the same procedures as described for whole blood except as modified by deproteinating the plasma by direct addition of concentrated $HNO_3$ [0.3 mL concentrated $HNO_3$+6 mL plasma (5% $HNO_3$)] with 4 mL of the deproteinated supernatant (SN1) being mixed with 0.8 mL of 12.8 M HCl before adding 4 mL of the sample to the column containing the anion exchange resin. The second centrifugation step was also not required for the plasma samples.

Tests for cadmium were carried out with 2 mL, 4 mL and 8 mL of plasma with two tests at each volume. The results are shown in Table IV below. The results (mean±standard error) at 2 mL level were 0.10±0.05 μg/L with a CV of 70%, at 4 mL were 0.10±0.02 μg/L with a CV of 25%, and at 8 mL were 0.06±0.01 with a CV of 20%. As shown, the standard error and CV decreased from 70% with the small volume to 20% with the larger volumes of test sample when the cadmium concentration in the test sample was low (0.06 μg Cd/L).

TABLE IV

Effect of Plasma Sample Volume on Assay Precision

| Sample volume | Cadmium concentration (μg/liter) | CV (%) |
|---|---|---|
| 2 ml | 0.10 ± 0.05(2) | 70 |
| 4 ml | 0.10 ± 0.02(2) | 25 |
| 8 ml | 0.06 ± 0.01(2) | 20 |

The donor was the sam for the blood and plasma samples of Exapmles I-VI as shown in Table III-IV. Therefore, information on the ratio of plasma Cd to blood Cd is significant and shows values ranging from 11-16%.

EXAMPLES VII-VIII

Urine samples (5 ml) were analyzed for cadmium using the procedures described above except as modified by direct acidification of urine with concentrated $HNO^3$ (instead of dilution with 1N $HNO_3$) with the results for five tests provided in Table V below.

TABLE V

Assay Characteristics - Precision and Accuracy

| | Cadmium concentration (μg/liter) | CV (%) | Cadmium added (ng) | Volume (ml) | Recovery % | Detection limit (μg Cd/liter) |
|---|---|---|---|---|---|---|
| | | | Intra-assay | | | |
| Blood | 0.57 ± 0.10(7) | 17 | — | 2-8 | — | 0.21 (2 ml) |
| | | | | | | 0.10 (4 ml) |
| | | | | | | 0.05 (8 ml) |
| | 0.32 ± 0.03(4) | 9 | — | 8 | — | 0.01 (8 ml) |
| Plasma | 0.09 ± 0.01(5) | 11 | — | 8 | — | 0.02 (8 ml) |
| Plasma + Spike | 0.27 ± 0.02(5) | 8 | 1.6 | 8 | 90 | 0.02 (8 ml) |
| Urine | 0.19 ± 0.05(5) | 26 | — | 5 | — | 0.02 (5 ml) |
| Urine + Spike | 0.76 ± 0.03(5) | 4 | 2.5 | 5 | 114 | 0.02 (5 ml) |
| | | | Interassay | | | |
| Blood | 0.61 ± 0.08(7) | 13 | — | 2 | — | 0.21 (2 ml) |
| Blood + Spike | 1.06 ± 0.10(6) | 9 | 1.0 | 2 | 90 | |
| Blood + Spike | 5.32 ± 0.27(6) | 5 | 10.0 | 2 | 94 | |

As shown in Table V the urine samples contained 0.19±0.05 μg Cd/L with a CV of 26%. The samples spiked with Cd (0.5 μg Cd/L) tested at 0.76±0.03 μg Cd/L with a CV of 4%. Comparisons between the two tests show an assay value for the spike of 0.57 μg Cd/L (0.76–0.19) which is within acceptable limits.

The foregoing description of embodiments of the invention has been presented for purposes of illustration and description. It is not intended to be exhaustive or to limit the invention to the precise form disclosed. Other modifications and variations are possible in light of the above teaching.

The embodiments of this invention in which an exclusive property or privilege is claimed are defined as follows:

1. A process for measuring half microgram levels of cadmium in biological fluids containing at least one alkali metal contaminant, comprising the steps of forming an aqueous solution of cadmium and the contaminant from a sample of the fluid converting the cadmium to anionic cadmium chloride selectively removing cadmium apart from a substantial portion of the contaminant from the aqueous solution on an anion exchange resin, resolubilizing cadmium from the resin to form a second solution, and analyzing for cadmium in the second solution, the process being carried out in an essentially cadmium-free environment.

2. The process of claim 1 wherein the analysis for cadmium is carried out by electrothermal atomic absorption.

3. The process of claim 1 including the step of increasing the cadmium content of the second solution by increasing the volume of the aqueous solution compared to the volume of the second solution.

4. The process of claim 1 wherein the fluid is blood, plasma or urine.

5. The process of claim 1 wherein the sample contains zinc and the process includes the step of increasing the analyzed value by a predetermined amount to correct for the limiting effect of Zn on the analyzed value for cadmium.

6. The process of claim 1 including the steps of adding a predetermined amount of $^{109}Cd$ to the sample before resolubilizing the sample cadmium from the resin and analyzing for $^{109}Cd$ as well as sample cadmium to provide a correlation between the analyzed sample cadmium with sample cadmium in the second solution.

7. The process of claim 1 including the step of selecting respective volumes of the aqueous and second solutions and the number of samples to provide a measure of cadmium content in the fluid with a coefficient of variation less than about 25%.

8. The process of claim 1 including the step of analyzing for blood and plasma to form a ratio separately for cadmium a patient useful in detecting recent exposure to harmful levels of cadmium.

9. A process for measuring half microgram levels of cadmium in biological fluids containing at least one alkali metal contaminant, comprising the steps of forming an aqueous solution of cadmium and the contaminant from a sample of the fluid, selectively removing cadmium apart from a substantial portion of the contaminant from the aqueous solution on an anion exchange resin, resolubilizing cadmium from the resin to form a second solution, and analyzing for cadmium in the second solution, the process being carried out in an essentially cadmium-free environment, the cadmium content of the second solution being increased by increasing the volume of the aqueous solution compared to the volume of the second solution, and a corrective factor for Zn being applied to correct for the limiting value of Zn on the analyzed value for cadmium.

* * * * *